United States Patent [19]

Arlt et al.

[11] 4,389,530
[45] Jun. 21, 1983

[54] PESTICIDALLY ACTIVE NOVEL PHOSPHORIC (PHOSPHONIC) ACID ESTER AMIDES

[75] Inventors: Dieter Arlt, Cologne; Bernhard Homeyer, Leverkusen; Ingeborg Hammann, Cologne, all of Fed. Rep. of Germany

[73] Assignee: Bayer Aktiengesellschaft, Leverkusen, Fed. Rep. of Germany

[21] Appl. No.: 352,723

[22] Filed: Feb. 26, 1982

[30] Foreign Application Priority Data

Mar. 18, 1981 [DE] Fed. Rep. of Germany ....... 3110596

[51] Int. Cl.$^3$ .................. C07F 7/08; C07F 7/18
[52] U.S. Cl. ................... 556/404; 119/156; 119/160; 43/124; 43/125; 43/132.1; 424/184
[58] Field of Search .............. 556/404; 424/184; 119/160, 156; 43/132 R, 124, 125

[56] References Cited

U.S. PATENT DOCUMENTS 2,864,845 12/1958 Kerschner et al. ............. 556/404
3,492,193 1/1970 Tesoro ..................... 556/404 X

FOREIGN PATENT DOCUMENTS 2629016 1/1978 Fed. Rep. of Germany .
415267 11/1974 U.S.S.R. .................. 556/404

OTHER PUBLICATIONS

Agricultural Chemistry, Section C, Apr. 4, 1979, p. 3.

*Primary Examiner*—Paul F. Shaver
*Attorney, Agent, or Firm*—Sprung, Horn, Kramer & Woods

[57] ABSTRACT

Pesticidally active novel phosphoric (phosphonic) acid ester amides have the general formula

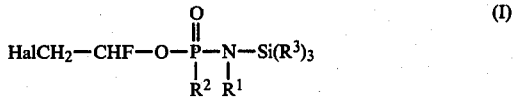

wherein
$R^1$ represents hydrogen or optionally substituted alkyl,
$R^2$ represents optionally substituted alkyl or optionally substituted alkoxy,
$R^3$ represents optionally substituted alkyl and
Hal represents halogen,
and are obtained if phosphoric (phosphonic) acid ester amides of the formula

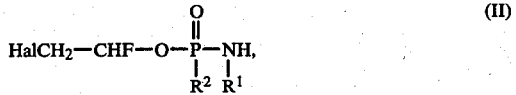

wherein
$R^1$, $R^2$ and Hal have the meanings given above, are reacted with trialkyl-chlorosilanes of the formula

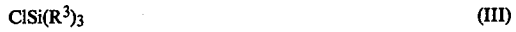

wherein
$R^3$ has the meaning given above, in the presence of an acid acceptor and, if appropriate, in the presence of a solvent. The compounds (I) can be used as pest-combating agents, particularly as insecticides and acaricides.

13 Claims, No Drawings

PESTICIDALLY ACTIVE NOVEL PHOSPHORIC (PHOSPHONIC) ACID ESTER AMIDES

The invention relates to certain new O-(1-fluoro-2-halogeno-ethyl)-phosphoric (phosphonic) acid ester amides, to a process for their preparation and to their use as pest combating agents.

It has already been disclosed in DE-Offenlegungsschrift (see United States Pat. No. 4,159,324) that certain phosphoric (phosphonic) acid ester amides have insecticidal, acaricidal and nematicidal properties. However, these compounds are not always completely satisfactory under certain conditions of use.

The present invention now provides, as new compounds, the phosphoric (phosphonic) acid ester amides of the general formula

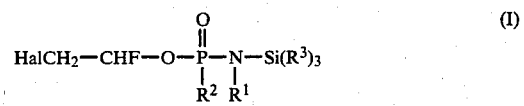

wherein

R$^1$ represents hydrogen or optionally substituted alkyl,

R$^2$ represents optionally substituted alkyl or optionally substituted alkoxy,

R$^3$ represents optionally substituted alkyl and Hal represents halogen.

The invention also provides a process for the preparation of a compound of the formula (I) in which a phosphoric (phosphonic) acid ester amide of the general formula

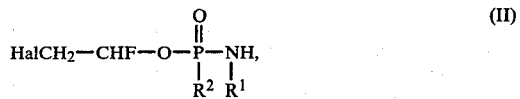

wherein

R$^1$, R$^2$ and Hal have the meanings given above, is reacted with a trialkyl-chlorosilane of the general formula

wherein

R$^3$ has the meaning given above, in the presence of an acid acceptor and, if appropriate, in the presence of a solvent.

Surprisingly, the compounds of the formula (I) are distinguished, in comparison to the corresponding compounds which are already known, particularly by a low level of toxicity to warm-blooded animals and particularly by a specific activity as a systemic soil insecticide of long duration of action. In addition, the compounds according to the invention are very well tolerated by plants.

In the optionally substituted alkyl groups R$^1$, R$^2$ and R$^3$, the alkyl moieties may be straight-chain or branched and preferably have 1 to 6, particularly 1 to 4, carbon atoms. Methyl, ethyl, n-propyl, i-propyl, n-butyl, i-butyl, s-butyl and t-butyl may be mentioned as examples.

In optionally substituted alkoxy groups R$^2$, the alkoxy moieties may be straight-chain or branched and preferably have 1 to 6, particularly 1 to 4, carbon atoms. Optionally substituted methoxy, ethoxy, n-propoxy, i-propoxy, n-butoxy, i-butoxy, s-butoxy and t-butoxy may be mentioned as examples.

The alkyl radicals R$^1$, R$^2$ and R$^3$ and the alkoxy radical R$^2$ can carry one or more, preferably 1 to 3, particularly 1 to 2, substituents, each of which is selected independently. The following may be quoted as examples of substitutents: alkoxy having preferably 1 to 4, particularly 1 to 2, carbon atoms, such as methoxy, ethoxy, n-propoxy, i-propoxy, n-butoxy, i-butoxy and t-butoxy; alkylthio having preferably 1 to 4, particularly 1 or 2, carbon atoms, such as methylthio, ethylthio, n-propylthio, i-propylthio, n-butylthio, i-butylthio and t-butylthio; halogen, preferably fluorine, chlorine, bromine and iodine, particularly chlorine and bromine; and cyano.

Halogen-substituted alkyl (halogenoalkyl) and alkoxy (halogenoalkoxy) may particularly be mentioned as the substituted alkyl R$^3$ and alkoxy R$^2$.

Hal preferably represents fluorine, chlorine, bromine and iodine, particularly chlorine and bromine.

Those compounds of the formula (I) are preferred wherein

R$^1$ represents hydrogen or alkyl,

R$^2$ represents alkyl, alkoxy or halogenoalkoxy,

R$^3$ represents alkyl or halogenoalkyl and

Hal represents chlorine or bromine.

Those compounds of the formula (I) are particularly preferred wherein

R$^1$ represents hydrogen or C$_{1-4}$-alkyl,

R$^2$ represents C$_{1-4}$-alkyl, C$_{1-4}$-alkoxy or C$_{1-4}$-halogenoalkoxy (having preferably 1 to 5, particularly 1 to 3, halogen atoms and preferably fluorine or chlorine as halogen), R$^3$ represents C$_{1-4}$-alkyl or C$_{1-4}$-halogenoalkyl (having preferably 1 to 5, particularly 1 to 3, halogen atoms and preferably fluorine or chlorine as halogen) and Hal represents chlorine or bromine.

Those compounds of the formula (I) are very particularly preferred in which

R$^1$ represents hydrogen, methyl, ethyl, i-propyl, n-propyl, 1-chloroisopropyl or sec.-butyl, R$^2$ represents C$_{1-4}$-alkyl or C$_{1-4}$-alkoxy, R$^3$ represents C$_{1-4}$-alkyl and Hal represents chlorine or bromine.

If, for example, O-[1-fluoro-2-bromo-ethyl]-O-ethylphosphoric acid diester N-ethylamide and trimethylmonochloro-silane are used as the starting materials, the reaction of these compounds can be represented by the following equation:

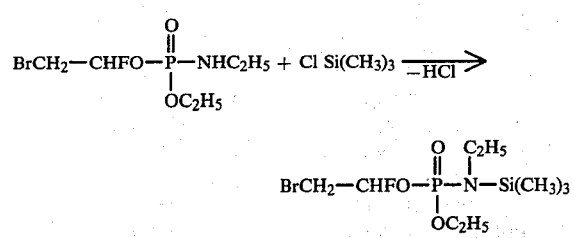

O-(1-Fluoro-2-halogeno-ethyl)-phosphoric (phosphonic) acid ester amides of the formula (II) used as starting materials are known and can be prepared in a customary manner by known processes.

The following may be mentioned as examples of these starting materials: methane- and ethane-O-(1-fluoro-2-chloro-ethyl)-phosphonic acid ester amide, methaneand ethane-O-(1-fluoro-2-bromo-ethyl)-phosphonic acid ester amide and their N-alkyl derivatives having 1 to 4 carbon atoms, and also O-(1-fluoro-2-chloro-ethyl)-O-methyl-phosphoric acid diester amide, O-(1-fluoro-2-chloro-ethyl)-O-methyl-phosphoric acid diester N-ethyl-amide, O-(1-fluoro-2-chloro-ethyl)-O-methyl-phosphoric acid diester N-methyl-amide, O-(1-fluoro-2-chloro-ethyl)-O-methyl-phosphoric acid diester N-i-propyl-amide, O-(1-fluoro-2-chloro-ethyl)-O-methyl-phosphoric acid diester N-n-propyl-amide, O-(1-fluoro-2-chloro-ethyl)-O-methyl-phosphoric acid diester N-sec.-butyl-amide, O-(1-fluoro-2-chloro-ethyl)-O-ethyl-phosphoric acid diester amide, O-(1-fluoro-2 -chloro-ethyl)-O-ethyl-phosphoric acid diester N-ethyl-amide, O-(1-fluoro-2-chloro-ethyl)-O-ethyl-phosphoric acid diester N-methyl-amide, O-(1-fluoro-2-chloro-ethyl)-O-ethyl-phosphoric acid diester N-i-propyl-amide, O-(1-fluoro-2-chloro-ethyl)-O-ethyl-phosphoric acid diester N-n-propyl-amide, O-(1-fluoro-2-chloro-ethyl)-O-ethyl-phosphoric acid diester N-sec.-butyl-amide, O-(1-fluoro-2-chloro-ethyl)-O-i- or n-propyl-phosphoric acid diester amide, O-(1-fluoro-2-chloro-ethyl)-O-i- or n-propyl-phosphoric acid diester N-ethyl-amide, O-(1-fluoro-2-chloroethyl)-O-i- or n-propyl-phosphoric acid diester N-methyl-amide, O-(1-fluoro-2-chloro-ethyl)-O-i- or n-propyl-phosphoric acid diester N-i-propyl-amide, O-(1-fluoro-2-chloro-ethyl)-O-i- or n-propyl-phosphoric acid diester N-n-propyl-amide, O-(1-fluoro-2-chloro-ethyl)-O-i- or n-propyl-phosphoric acid diester N-sec.-butyl-amide, O-(1-fluoro-2-bromo-ethyl)-O-methyl-phosphoric acid diester amide, O-(1-fluoro-2-bromo-ethyl)-O-methyl-phosphoric acid diester N-ethyl-amide, O-(1-fluoro-2-bromo-ethyl)-O-methyl-phosphoric acid diester N-methyl-amide, O-(1-fluoro-2-bromo-ethyl)-O-methyl-phosphoric acid diester N-i-propyl-amide, O-(1-fluoro-2-bromo-ethyl)-O-methyl-phosphoric acid diester N-n-propyl-amide, O-(1-fluoro-2-bromo-ethyl)-O-methyl-phosphoric acid diester N-sec.-butyl-amide, O-(1-fluoro-2-bromo-ethyl)-O-ethyl-phosphoric acid diester N-amide, O-(1-fluoro-2-bromo-ethyl)-O-ethyl-phosphoric acid diester N-ethyl-amide, O-(1-fluoro-2-bromo-ethyl)-O-ethyl-phosphoric acid diester N-methyl-amide, O-(1-fluoro-2-bromo-ethyl)-O-ethyl-phosphoric acid diester N-i-propyl-amide, O-(1-fluoro-2-bromo-ethyl)-O-ethyl-phosphoric acid diester N-n-propyl-amide, O-(1-fluoro-2-bromo-ethyl)-O-ethyl-phosphoric acid diester N-sec.-butyl-amide and O-(1-fluoro-2-bromo-ethyl)-O-ethyl-phosphoric acid diester N-chloro-isopropyl-amide.

The reaction of the starting materials of the formula (II) and (III) to give the compounds of the formula (I) is preferably carried out concomitantly using a suitable solvent or diluent. Virtually any of the inert organic solvents are suitable solvents and diluents. These include, as preferences, aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

Any of the customary acid-binding agents can be used as the acid acceptor. Tertiary amines, such as trimethylamine, triethylamine, dimethylaniline, dimethylbenzylamine and pyridine, and alkali metal carbonates, such as sodium carbonate and potassium carbonate, have proved particularly suitable.

The reaction temperature can be varied within a relatively wide range. In general, the reaction is carried out at a temperature of between 0° and 100° C., preferably at from 20° to 40° C. The reaction is generally allowed to proceed under normal pressure. The reactants are preferably employed in an equimolar ratio. An excess of one the other of the reactants gives no substantial advantages. The reaction is preferably carried out in one of the solvents indicated, in the presence of an acid acceptor. The working-up of the mixture may be effected, according to customary methods, by filtering, washing the filtrate and distilling off the solvent.

The present compounds are obtained in the form of oils, which cannot be distilled without decomposition, but can be freed from the last volatile constituents by so-called "incipient distillation", that is to say by prolonged heating to moderately elevated temperatures under reduced pressure, and can be purified in this manner. They can be characterized by their refractive index.

The active compounds are well tolerated by plants, have a favorable level of toxicity to warm-blooded animals, and are suitable for combating arthropod pests, especially insects and arachnids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium*

*corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysis ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., Oryzaephilus surinamensis, Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha. Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit.* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp.

The active compounds can be converted into the customary formulations, such as solutions, emulsions, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in their formulations of the types that are commercially available and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by micro-organisms.

The active compounds according to the invention can furthermore be present in their formulations of the types that are commercially available and in the use forms, prepared from these formulations, as a mixture with synergistic agents. Synergistic agents are compounds which increase the action of the active compounds, without it being necessary for the synergistic agent added to be active itself.

The active compound content of the use forms prepared from the formulations of the types that are commercially available can vary within wide limits. The active compound concentration of the use forms can be from 0.0000001 to 100% by weight of active compound, preferably between 0.0001 and 1% by weight.

The compounds are employed in a customary manner appropriate for the use forms.

When used against pests harmful to health and pests of stored products, the active compounds are distinguished by an excellent residual action on wood and clay as well as a good stability to alkali on limed substrates.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests, especially arthropods (such as insects or acarids) or nematodes, which comprises applying to the pests, or to a habitat thereof, a compound of the present invention alone or in the form of a composition containing as active ingredient a compound of the present invention in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The examples which follow are intended to illustrate the process for the preparation of the compounds according to the invention (Me denotes CH₃):

EXAMPLE 1

27.8 g (0.1 mol) of O-[1-fluoro-2-bromo-ethyl]-O-ethyl-phosphoric acid diester N-ethyl-amide and 13.0 g of trimethyl-monochloro-silane (0.12 mol) were dissolved in 150 ml of toluene. 12.0 g (0.12 mol) of triethylamine were added dropwise to the solution at 20°–25° C. The reaction mixture was stirred for 5 hours and was then extracted in a shaking funnel twice with 250 ml of water. The organic phase was dried with sodium sulphate and the solvent was evaporated in vacuo. 32.5 g of crude O-[1-fluoro-2-bromo-ethyl]-O-ethyl-phosphoric acid diester N-ethyl-N-trimethylsilyl-amide were obtained as a pale brown oil; $n_D^{20}$: 1.4514.

EXAMPLE 2

21.0 g (0.1 mol) of O-[1-fluoro-2-chloro-ethyl]-O-methyl-phosphoric acid diester N-ethyl-amide and 13.0 g (0.12 mol) of trimethyl-monochlorosilane were dissolved in 150 ml of methylene chloride. 12.0 g (0.12 mol) of triethylamine were added dropwise to the solution at 10°–20° C., while stirring. After 6 hours, the reaction mixture was stirred with 500 ml of water. The phases were separated and, subsequently, the methylene chloride solution of the active compound formed was dried with sodium sulphate and concentrated in vacuo. 27 g of crude O-[1-fluoro-2-chloro-ethyl]-O-methyl-phosphoric acid diester N-ethyl-N-trimethylsilylamide, a colored oil, remained; $n_D^{20}$: 1.4451.

The following compounds were synthesised in a manner analogous to that described in Example 1 or 2, and were characterized by their refractive indices:

Compound 3

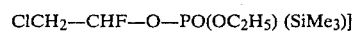

$n_D^{20}$: 1.4387

Compound 4

$n_D^{20}$: 1.4358

Compound 5

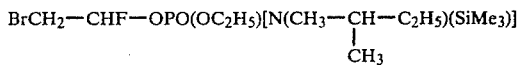

$n_D^{20}$: 1.4543

Compound 6

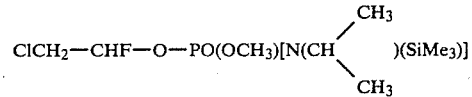

$n_D^{20}$: 1.4408

The activity of the compounds of this invention is illustrated by the following examples wherein the compounds according to the present invention are each identified by the compound number (given in brackets) from the preparative examples hereinabove.

A comparison was made in some cases with O-[1-fluoro-2-bromoethyl]-O-ethyl-phosphoric acid diester N-ethylamide ("comparison compound A") and O-[1-fluoro-2-chloroethyl]-O-ethyl-phosphoric acid diester N-methylamide ("comparison compound B") which are known from the DE-Offenlegungsschrift (Unites States Pat. No. 4,159,324).

EXAMPLE 3

Critical concentration test / soil insects
Test insect: Phorbia antiqua maggots (in the soil)
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil. The concentration of the active compound in the preparation was of practically no importance, only the amount by weight of active compound per unit volume of soil, given in ppm (=mg/l), being decisive. The soil was filled into pots and the pots were left to stand at room temperature.

After 24 hours, the test insects were introduced into the treated soil, and after 2 days the degree of effectiveness of the active compound was determined in % by counting the dead and the live test insects. The degree of effectiveness was 100% if all the test insects had been killed and was 0% if just as many test insects were still alive as in the case of the untreated control.

In a test at an active compound concentration of 1.25 ppm, the "comparison compound A" showed no action (0%), whereas the compounds (1), (2), (3) and (4), for example, showed a degree of effectiveness of 100%.

EXAMPLE 4

Critical concentration test / nematodes
Test nematode: Meloidogyne incognita
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance, only the amount of active compound per unit volume of soil, given in ppm, being decisive. The treated soil was filled into pots, lettuce was sown in and the pots were kept at a greenhouse temperature of 27° C.

After four weeks, the lettuce roots were examined for infestation with nemotodes (root galls), and the degree of effectiveness of the active compound was determined in %. The degree of effectiveness was 100% if infestation was completely avoided and was 0% if the infestation was just as high as in the case of the control plants in untreated soil which had been infested in the same manner.

In a test at a concentration of 5 ppm, the compounds (1), (2), (3), (4) and (5), for example, showed a degree of effectiveness of 100%.

EXAMPLE 5

Tetranychus test (resistant)
Solvent: 3 parts by weight of acetone
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Phaseolus vulgaris*) which were heavily infested with the common spider mite or two-spotted spider mite (*Tetranychus urticae*) in all stages of development were treated by being dipped into the preparation of the active compound of the desired concentration.

After the specified periods of time, the destruction in % was determined. 100% meant that all the spider mites had been killed; 0% meant that none of the spider mites had been killed.

In a test at a concentration of 0.1%, the "comparison compound A" showed a degree of destruction of 40% after 2 days, whereas the compounds (1), (2) and (4), for example, gave degrees of destruction between 95 and 100%.

EXAMPLE 6

Drosophila test
Solvent: 3 parts by weight of acetone
Emulsifier: 1 part by weight of alkylaryl polyglycol To produce a suitable preparation of active compound, 1 part by weight of active compound was mixed with the stated amount of solvent and the stated amount of emulsifier, and the concentrate was diluted with water to the desired concentration.

1 cm$^3$ of the preparation of the active compound was pipetted onto a filter paper disc (7 cm diameter). The wet disc was placed over the opening of a glass vessel containing 50 vinegar flies (*Drosophila melanogaster*) and was covered with a glass plate.

After the specified periods of time, the destruction in % was determined. 100% meant that all the flies had been killed; 0% meant that none of the flies had been killed.

In this test, at concentrations of 0.001%, the comparison compounds A and B showed no action (0%) after 1 day, whereas the compounds (1), (2) and (3), for example, gave a degree of destruction of 100% and the compound (4) gave a degree of destruction of 95%.

It will be understood that the specification and examples are illustrative but not limitative of the present invention and that other embodiments within the spirit and scope of the invention will suggest themselves to those skilled in the art.

We claim:

1. A phosphoric (phosphonic) acid ester amide of the formula

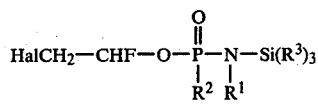

wherein
R$^1$ is hydrogen or optionally substituted alkyl,
R$^2$ is optionally substituted alkyl or optionally substituted alkoxy,
R$^3$ is optionally substituted alkyl, and
Hal is halogen.

2. A compound according to claim 1, in which
R$^1$ is hydrogen or alkyl
R$^2$ is alkyl, alkoxy or halogenoalkoxy,
R$^3$ is alkyl or halogenoalkyl, and
Hal is chlorine or bromine.

3. A compound according to claim 1 in which
R$^1$ is hydrogen or C$_{1-4}$-alkyl,
R$^2$ is C$_{1-4}$-alkyl, C$_{1-4}$-alkoxy or C$_{1-4}$-halogenoalkoxy having 1 to 5 halogen atoms,
R$^3$ is C$_{1-4}$-alkyl or C$_{1-4}$-halogenoalkyl having 1 to 5 halogen atoms, and
Hal is chlorine or bromine.

4. A compound according to claim 1, in which
R¹ is hydrogen, methyl, ethyl, i-propyl, n-propyl, 1-chloroisopropyl or sec.-butyl,
R² is $C_{1-4}$-alkyl or $C_{1-4}$-alkoxy and
Hal is chlorine or bromine.

5. A compound according to claim 1, wherein such compound is O-[1-fluoro-2-bromo-ethyl]-O-ethyl-phosphoric acid diester N-ethyl-N-trimethylsilyl-amide of the formula
    $BrCH_2-CHF-O-PO(OC_2H_5)[N(C_2H_5)(SiMe_3)]$ in which Me is methyl.

6. A compound according to claim 1, wherein such compound is O-[1-fluoro-2-chloro-ethyl]-O-methyl-phosphoric acid diester N-ethyl-N-trimethylsilyl-amide of the formula
    $ClCH_2-CHF-O-PO(OCH_3)[N(C_2H_5)(SiMe_3)]$ in which Me is methyl.

7. A compound according to claim 1, wherein such compound is O-[1-fluoro-2-chloro-ethyl]-O-ethyl-phosphoric acid diester N-ethyl-N-trimethylsilyl-amide of the formula $ClCH_2-CHF-O-PO(OC_2H_5)[N(C_2H_5)(SiMe_3)]$ in which Me is methyl.

8. A compound according to claim 1, wherein such compound is
O-[1-fluoro-2-chloro-ethyl]-O-ethyl-phosphoric acid diester N-methyl-N-trimethylsilyl-amide of the formula $ClCH_2-CHF-OPO(OC_2H_5)[N(CH_3)SiMe_3)]$ in which Me is methyl.

9. A compound according to claim 1, wherein such compound is O-[1-fluoro-2-bromo-ethyl]-O-ethyl-phosphoric acid diester N-(2-methyl-butyl)-N-trimethylsilyl-amide of the formula $$BrCH_2-CHF-OPO(OC_2H_5)[N(CH_3-CH-C_2H_5)(SiMe_3)]$$
$$|$$
$$CH_3$$

in which Me is methyl.

10. A compound according to claim 1, wherein such compound is O-[1-fluoro-2-chloro-ethyl]-O-methyl-phosphoric acid diester N-isopropyl-N-trimethylsilyl-amide of the formula $$ClCH_2-CHF-O-PO(OCH_3)[N(CH(CH_3)_2)(SiMe_3)]$$

in which Me is methyl.

11. A pesticidal composition comprising a pesticidally effective amount of a compound according to claim 1 in admixture with a diluent.

12. A method of combating arthropods and nematodes comprising applying to the arthropods or nematodes, or to a habitat thereof, an arthropodicidally or nematocidally effective amount of a compound according to claim 1.

13. The method according to claim 12, wherein such compound is
  O-[1-fluoro-2-bromo-ethyl]-O-ethyl-phosphoric acid diester N-ethyl-N-trimethylsilyl-amide,
  O-[1-fluoro-2-chloro-ethyl -O-methyl-phosphoric acid diester N-ethyl-N-trimethylsilyl-amide,
  O-[1-fluoro-2-chloro-ethyl]-O-ethyl-phosphoric acid diester N-ethyl-N-trimethylsilyl-amide,
  O-[1-fluoro-2-chloro-ethyl]-O-ethyl-phosphoric acid diester N-methyl-N-trimethylsilyl-amide,
  O-[1-fluoro-2-bromo-ethyl]-O-ethyl-phosphoric acid diester N-(2-methyl-butyl)-N-trimethylsilyl-amide or
  O-[1-fluoro-2-chloro-ethyl]-O-methyl-phosphoric acid diester N-isopropyl-N-trimethylsilyl-amide.

* * * * *

UNITED STATES PATENT AND TRADEMARK OFFICE
CERTIFICATE OF CORRECTION

PATENT NO. : 4,389,530
DATED : June 21, 1983
INVENTOR(S) : Dieter Arlt et al

It is certified that error appears in the above-identified patent and that said Letters Patent is hereby corrected as shown below:

Col. 2, line 5      Delete "to" and insert --or--
Col. 2, line 8      Delete "to" and insert --or--
Col. 5, line 17      Delete "Clysis" and insert --Clysia--
Col. 8, line 20      After "($OC_2H_5$)" insert --[N($C_2H_5$)--

Signed and Sealed this

Fourth Day of October 1983

[SEAL]

Attest:

GERALD J. MOSSINGHOFF

Attesting Officer     Commissioner of Patents and Trademarks